US006589528B2

(12) United States Patent
Ito et al.

(10) Patent No.: US 6,589,528 B2
(45) Date of Patent: Jul. 8, 2003

(54) METHOD FOR INDUCTION OF DIFFERENTIATION OF OSTEOCLASTS

(75) Inventors: Yasuhiko Ito, Mie (JP); Shigeomi Higuchi, Mie (JP)

(73) Assignee: DNAVEC Research Inc., Ibaraki (JP)

( * ) Notice: Subject to any disclaimer, the term of this patent is extended or adjusted under 35 U.S.C. 154(b) by 0 days.

(21) Appl. No.: 09/993,076

(22) Filed: Nov. 6, 2001

(65) Prior Publication Data

US 2002/0031514 A1 Mar. 14, 2002

Related U.S. Application Data

(63) Continuation of application No. 09/099,174, filed on Jun. 18, 1998, now abandoned.

(30) Foreign Application Priority Data

Jan. 8, 1998 (JP) ............................................ 10-14788

(51) Int. Cl.[7] .............................................. A61K 39/395
(52) U.S. Cl. ................................. 424/143.1; 424/142.1
(58) Field of Search .......................... 530/388.2, 388.7; 435/7.1; 424/142.1, 143.1

(56) References Cited

U.S. PATENT DOCUMENTS 5,196,192 A 3/1993 De Kretser et al.

OTHER PUBLICATIONS

Higuchi et al., "Formation of Osteoclasts from Blood Monocytes by Anti–Fusion Regulatory Protein–1/CD98 Monoclonal Antibody," *Journal of the Japanese Society for Bone and Mineral Research* 15(2):70 (1997).

Higuchi et al., "Induction of Human Osteoclast–like Cells by Treatment of Blood Monocytes with Anti–Fusion Regulatory Protein–1/CD98 Monoclonal Antibodies," *J. Bone Miner. Res.,* 13:44–49 (1998).

Ikegame et al., "Effects of Continuous Calcitonin Treatment on Osteoclast–Like Cell Development and Calcitonin Receptor Expression in Mouse Bone Marrow Cultures," *J. Bone Miner. Res.,* 11:456–465 (1996).

Kotake et al., "IL–17 in Synovial Fluids from Patients with Rheumatoid Arthritis Is a Potent Stimulator of Osteoclastogenesis," *J. Clin. Invest.,* 103:1345–1352 (1999).

Kukita et al., "Osteoclast–Like Cells Formed in Long–Term Human Bone Marrow Cultures Express a Similar Surface Phenotype as Authentic Osteoclasts," *Lab. Invest.,* 60:532–538 (1989).

Kurihara et al., "Identification of Committed Mononuclear Precursors for Osteoclast–Like Cells Formed in Long Term Human Marrow Cultures," *Endo.,* 126:2733–2741 (1990).

Kurihara et al., "Sequential Expression of Phenotype Markers for Osetoclasts During Differentiation of Precursors for Multinucleated Cells Formed in Lone Term Human Marrow Cultures," *Endo.,* 127:3215–3221 (1990).

Mbalaviele et al., "Osteoclast Formation from Human Cord Blood Mononuclear Cells Co–Cultured with Mice Embryonic Metatarsals in the Presence of M–CSF," *Bone* 16:171–177 (1995).

MacDonald et al., "Formation of Multinucleated Cells that Respond to Osteotropic Hormones in Long Term Human Bone Marrow Cultures," *Endo.,* 120:2326–2333 (1987).

Matsuzaki et al., "Osteoclast Differentiation Factor (ODF) Induces Osteoclast–Like Cell Formation in Human Peripheral Blood Mononuclear Cell Cultures," *Biochem. Biophys. Res. Commun.,* 246:199–204 (1998).

Matsuzaki et al., "Human Osteoclast–Like Cells Are Formed from Peripheral Blood Mononuclear Cells in a Coculture with SaOS–2 Cells Transfected with the Parathyroid Hormone (PTH)/PTH–Related Protein Receptor Gene," *Endo.,* 140:925–932 (1999).

Miyahara et al., "Effects of Lead on Osteoclast–Like Cell Formation in Mouse Bone Marrow Cell Cultures," *Calcif. Tissue Int.,* 54:165–169 (1994).

Ohgimoto et al., "Molecular Characterization of Fusion Regulatory Protein–1 (FRP–1) that Induces Multinucleated Giant Cell Formation of Monocytes and HIV gp160–Mediated Cell Fusion," *J. Immunol.,* 155:3858–3592 (1995).

Okamato et al., "Paramyxovirus–Induced Syncytium Cell Formation Is Suppressed by a Dominant Negative Fusion Regulator Protein–1 (FRP–1)/CD98 Mutated Construct: An Important Role of FRP–1 in Virus–Induced Cell Fusion," *J. Gen. Virol.,* 78:775–783 (1997).

Purton et al., "Normal Human Peripheral Blood Mononuclear Cells Mobilized with Granulocyte Colony–Stimulating Factor Have Increased Osteoclastogenic Potential Compared to Nonmobilized Blood," *Blood* 87:1802–1808 (1996).

Quinn et al., "Rodent Osteoblast–Like Cells Support Osteoclastic Differentiation of Human Cord Blood Monocytes in the Presence of M–CSF and 1,25 Dihydroxyvitamin $D_3$," *Int. J. Biochem. Cell. Biol.,* 29:173–179 (1997).

Quinn et al., "Human Osteoclast Formation from Blood Monocytes, Peritoneal Macrophages, and Bone Marrow Cells," *Calcif. Tissue Int.,* 62:527–531 (1998).

(List continued on next page.)

*Primary Examiner*—Sheela Huff
(74) *Attorney, Agent, or Firm*—Clark & Elbing LLP

(57) ABSTRACT

The present invention provides a simple method of producing osteoclasts from monocytes, a agent comprising monoclonal antibody to be used for the method, and a method for screening a ligand that induces differentiation of monocytes to osteoclasts. Differentiation of monocytes to osteoclasts can be induced in vitro by culturing isolated human peripheral blood monocytes in the presence of monoclonal antibody that binds to a portion of FRP-1 protein exposed on the surface of monocytes. Such a differentiation system can be utilized to isolate a ligand that binds to FRP-1 protein and induces differentiation of monocytes to osteoclasts.

2 Claims, 5 Drawing Sheets

OTHER PUBLICATIONS

Ransjö et al., "Cholera Toxin and Forskolin Stimulate Formation of Osteoclast–Like Cells in Mouse Marrow Cultures and Cultured Mouse Calvarial Bones," *Eur. J. Oral. Sci.,* 107:45–54 (1999).

Roux et al., "Effects of Prostaglandins on Human Hematopoietic Osteoclast Percursors," *Endo.,* 138:1476–1482 (1997).

"Stedman's Medical Dictionary, $24^{th}$ Edition," Williams & Wilkins, p. 1118 (1982).

Suga et al., "Identification of Fusion Regulatory Protein (FRP)–1/4FR Related Molecules: Cytoskeletal Proteins Are Associated with FRP–1 Molecules that Regulate Multinucleated Giant Cell Formation of Monocytes and HIV–Induced Cell Fusion," *Cell Stucture and Function* 20:473–483 (1995).

Suga et al., "Human Immunodeficiency Virus Type–1 Envelope Glycoprotein gp120 Induces Expression of Fusion Regulatory Protein (FRP)–1/CD98 on CD4 T Cells: A Possible Regulatory Mechanism of HIV–Induced Syncytium Formation," *Med. Microbiol. Immunol.,* 185:237–243 (1997).

Tabata et al., "Expression of Fusion Regulatory Proteins (FRPs) on Human Peripheral Blood Monocytes," *J. Immunol.,* 153:3256–3266 (1994).

Tabata et al., "Protein Tyrosine Kinase Activation Provides an Early and Obligatory Signal in Anti–FRP–1/CD98/4F2 Monoclonal Antibody Induced Cell Fusion Mediated by HIV gp160," *Med. Microbiol. Immunol.,* 186:115–123 (1997).

Takahashi et al., "Induction of Calcitonin Receptors by 1–60, 25–Dihydroxyvitamin $D_3$ in Osteoclast–Like Multinucleated Cells Formed from Mouse Bone Marrow Cells," *Endo.,* 123:1504–1510 (1988).

Takahashi et al., "Role of Colony–Stimulating Factors in Osteoclast Development," *J. Bone Miner. Res.,* 6:977–985 (1991).

Takahashi et al., "Development and Characterization of a Human Marrow Stromal Cell Line that Enhances Osteoclast–Like Cell Formation," *Endo.,* 136:1441–1449 (1995).

Tamura et al., "Soluble Interleukin–6 Receptor Triggers Osteoclast Formation by Interleukin 6," *Proc. Natl. Acad. Sci., USA* 90:11924–11928 (1993).

Tsumura et al., "Mouse Alloantigen Ly10 is Identical to Murine Fusion Regulatory Protein–1 (mFRP–1)/4F2/CD98: Aberrant Expression of mFRP–1/Ly10 Allotypes in Cells Derived from CDF–1 Mice Due to the Deletion," *Cellular Immunol.,* 184:153–160 (1998).

Tsumura et al., "Isolation and Characterization of Monoclonal Antibodies Directed Against Murine FRP–1/CD98/4F2 Heavy Chain: Murine FRP–1 Is an Alloantigen and Amino Acid Change at 129 (P←→R) Is Related to the Alloantigenicity," *Immunol. Cell. Biol.,* 77:19–27 (1999).

Tsurudome et al., "Cutting Edge: Primary Structure of the Light Chain of Fusion Regulatory Protein–1/CD98/4F2 Predicts a Protein with Multiple Transmembrane Domains that Is Almost Identical to the Amino Acid Transporter E16," *J. Immunol.,* 162:2462–2466 (1999).

Udagawa et al., "Origin of Osteoclast: Mature Monocytes and Macrophages Are Capable of Differentiating into Osteoclasts under a Suitable Microenvironment Prepared by Bone Marrow–Derived Stromal Cells," *Proc. Natl. Acad. Sci. USA* 87:7260–7264 (1990).

Vignery, "Osteoclasts and Giant Cells: Macrophage–Macrophage Fusion Mechanism," *Intl. J. Exp. Pathol.,* 81:291–304 (2000).

Yamashita et al., "Cloning of an Osteoblastic Cell Line Involved in the Formation of Ostoeclast–Like Cells," *J. Cell Physiol.,* 145:587–595 (19900.

Yoneda et al., "Differentiation of HL–60 Cells into Cells with the Osteoclast Phenotype," *Endo.,* 129:683–689 (1991).

Akatsu et al., "Chinese Hamster Ovary Cells Expressing $\alpha_4\beta_1$ Integrin Stimulate Osteoclast Formation In Vitro," *J. Bone Miner. Res.*, 13:1251–1259 (1998).

Amano et al., "Colony–Stimulating Factor–1 Stimulates the Fusion Process in Osteoclasts," *J. Bone. Miner. Res.*, 13:846–853 (1998).

Aoki et al., "Transient Expression of M–CSF Is Important for Osteoclast–Like Cell Differentiation in a Monocytic Leukemia Cell Line," *J. Cell. Biochem.*, 64:67–76 (1997).

Collin–Osdoby et al., "Osteoclast 121F Antigen Expression during Osteoblast Conditioned Medium Induction of Osteoclast–Like Cells In Vitro: Relationship to Calcitonin Responsiveness, Tartrate Resistant Acid Phosphatase Levels, and Bone Resorptive Activity," *J. Bone Miner. Res.*, 10:45–58 (1995).

Fujikawa et al.,"Human Osteoclast Formation and Bone Resorption by Monocytes and Synovial Macrophages in Rheumatoid Arthritis," *Ann. Rheum. Dis.*, 55:816–822 (1996).

Fujikawa et al., "The Human Osteoclast Precursor Circulates in the Monocyte Fraction," *Endo.*, 137:4058–4060 (1996).

Galvin et al., "Development and Characterization of a Porcine Model to Study Osteoclast Differentiation and Activity," *Bone* 19:271–279 (1996).

Han et al., CD47, a Ligand for the Macrophage Fusion Receptor, Participates in Macrophage Multinucleation, *J. Biol. Chem.*, 275:37984–37992 (2000).

Hentunen et al., "Effects of Recombinant Human Osteogenic Protein–1 on the Differentiation of Osteoclast–Like Cells and Bone Resorption," *Biochem. Biophys. Res. Commun.*, 209:433–443 (1995).

Heymann et al., "Upmodulation of Multinucleated Cell Formation in Long–Term Human Bone Marrow Cultures by Leukaemia Inhibitory Factor (LIF)," *Cytokine* 9:46–52 (1997).

Heymann et al., "Oncostatin M Stimulates Macrophage–Polykaryon Formation in Long–Term Human Bone–Marrow Cultures," *Cytokine* 10:98–109 (1998).

METHOD FOR INDUCTION OF DIFFERENTIATION OF OSTEOCLASTS

PRIORITY INFORMATION

This application is a continuation of, and claims priority from, U.S. patent application Ser. No. 09/099,174, filed on Jun. 18, 1998, and abandoned, which in turn claims priority from Japanese Patent Application HEI 10-14788, filed on Jan. 8, 1998.

FIELD OF THE INVENTION

The present invention relates to a method for induction of differentiation of monocytes to osteoclasts, an agent comprising monoclonal antibody used for the above method, and a method for screening a ligand that induces differentiation of monocytes to osteoclasts.

BACKGROUND OF THE INVENTION

It is known that osteoclasts are multinucleated giant cells involved in bone resorption and have their origin in hematopoietic system (Udagawa, N. et al., Proc. Natl. Acad. Sci. USA 87: 7260–7264 (1990)). Although precise mechanisms for their differentiation and activation are not clear at present, osteoclasts are one of the most important factors that participate in the physiological metabolism of the bone and abnormality of these cells is related with osteoporosis. Formation of multinucleated cells induced by membrane fusion is the first step of formation of osteoclasts. Membrane fusion is an important process in biological phenomena (White, J. M., Annu. Rev. Physiol. 52: 675–697 (1990), Burger, K. N. and Verkleij, A., J. Experientia 46: 631–644 (1990)). Membrane fusion is also involved in fertilization, formation of muscles, exocytosis, endocytosis, formation of organella, and transport between intracellular organella. However, mechanisms that control membrane fusion is not well understood yet.

It has been reported that interstitial cells and steroids such as 1a, 25-dihydroxyvitamin $D_3$ or parathyroid hormone are necessary for formation of multinucleated osteoclasts caused by fusion of mononuclear cells of macrophages/monocytes (Takahashi, N. et al., Endocrinol. 122: 1373–1382 (1988), Takahashi, N. et al., Endocrinol. 123: 1504–1510 (1988), Quinn, J. M. W. et al., The Endocrin. Soc. 134: 2416–2423 (1991)). It has also been reported that several kinds of cytokines induce the formation of multinucleated cells from monocytes/macrophages (Lacey D. L. et al., Endocrinol. 136: 2367–2376 (1995), Murray G. R. J., Bone and Miner. Res. 8: S505–S510 (1993)). However, these methods do not clearly demonstrate that derived cells perform bone resorption. Furthermore, these methods require the presence of stroma cells and, thus, are not simple. There has been no report pertaining to a method of in vitro induction and differentiation of osteoclasts.

SUMMARY OF THE INVENTION

An object of the present invention is to provide a simple method for production of osteoclasts from monocytes, a agent comprising monoclonal antibody used in this method, and a method for screening of a ligand that induces differentiation of monocytes to osteoclasts. To achieve the object, the present inventors ardently studied and succeeded for the first time in differentiation of monocytes to osteoclasts in vitro by culturing isolated monocytes in the presence of monoclonal antibodies that bind to FRP-1 protein present on the surface of monocytes. Furthermore, the present inventors found that it was possible to isolate a ligand that binds to FRP-1 protein and induces differentiation of monocytes to osteoclasts with the use of the system for differentiation of monocytes to osteoclasts.

Thus, the present invention relates to a simple method for induction of differentiation of monocytes to osteoclasts using monoclonal antibody capable of inducing differentiation of monocytes to osteoclasts, an agent comprising the monoclonal antibody, and a method for screening a ligand that induces differentiation of monocytes to osteoclasts. More specifically, the present invention relates to (1) a method of producing osteoclasts which comprises a step of contacting monocytes with monoclonal antibody that binds to a portion of FRP-1 protein exposed on the surface of monocytes;

(2) the method according to (1), wherein the osteoclasts are cells cultured in vitro;

(3) the in vitro cultured cells of osteoclasts obtainable by contacting monocytes with monoclonal antibody that binds to a portion of FRP-1 protein exposed on the surface of monocytes;

(4) the in vitro cultured cells according to (3), which is derived from human;

(5) an agent for inducing differentiation of monocytes to osteoclasts which comprises monoclonal antibody that binds to a portion of FRP-1 protein exposed on the surface of monocytes as an active ingredient;

(6) a method for screening a ligand that binds to FRP-1 protein, which comprises steps of treating monocytes with a test sample and detecting differentiation of monocytes to osteoclasts;

(7) a ligand that binds to FRP-1 protein and can be isolated by the method according to (6).

(8) the ligand according to (7), which is a naturally-occurring substance.

BRIEF DESCRIPTION OF THE DRAWINGS

FIG. 3 shows calcitonin receptors on the surface of multinucleated giant cells. Blood monocytes were cultured in the presence of anti-FRP-1 monoclonal antibody (6-1-13; 1 mg/ml) and the cells were treated with (a) labeled calcitonin in the presence of excess non-labeled calcitonin or (b) labeled calcitonin in the absence of excess non-labeled calcitonin (magnification ×1000).

In FIG. 4*a*, monocytes were cultured on the human cortical bone slices in the presence of anti-FRP-1 monoclonal antibody to measure bone, while, in FIG. 4*b*, monocytes were cultured on the human cortical bone slices in the absence of anti-FRP-1 monoclonal antibody to measure bone resorption (magnification ×100).

FIG. 5 shows detection of FRP-1 antibody on the osteoclasts isolated from human bone fragment. FIG. 5*a* shows human osteoclasts isolated from the TRAP-positive and multinucleated bone fragment.

FIG. 5*b* shows human osteoclasts fixed with paraformaldehyde and stained with anti-FRP-1 antibody (4-5-1) (magnification ×600).

DETAILED DESCRIPTION OF THE INVENTION

Figure 1:
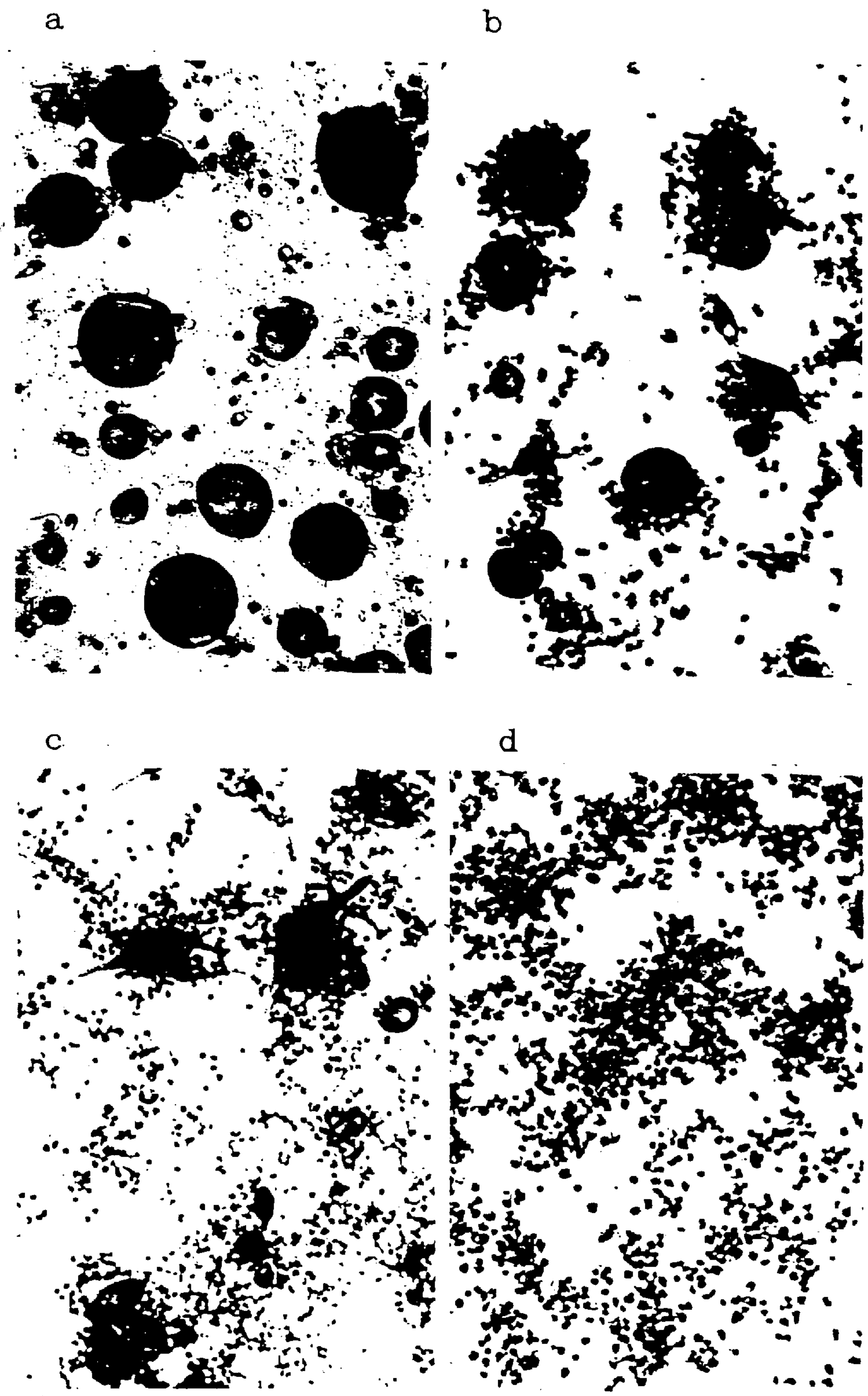
FIG. 1 shows the induction of multinucleated giant cells by contacting monocytes with anti-FRP-1 antibody. The antibodies used were anti-FRP-1 monoclonal antibody 6-1-13 in (a), anti-FRP-1 monoclonal antibody 4-5-1 in (b), anti-FRP-1 monoclonal antibody 4F2 in (c), and isotype compatible control antibody in (d). Giemsa staining was effected in each case (magnification ×600).

The term "monocytes" used herein means precursor cells of macrophage cells, which are mobile, amoeba-like phagocytes having a diameter of about 10 μm present in the blood. The term "osteoclasts" means the cells capable of performing bone resorption and having such properties as being multinucleated and resistant to tartaric acid. The term "ligand" means the compound that binds to a portion of FRP-1 protein exposed on the surface of monocytes and induces differentiation of the monocytes to osteoclasts. Such a ligand includes artificially synthesized compounds as well as naturally-occurring compounds such as proteins (including antibodies), peptides, gene expression products (including cDNA libraries), non-peptide compounds, extracts from tissues or cells, and the like.

The present invention relates to a method of producing osteoclasts from monocytes using monoclonal antibody binding to FRP-1 protein. The present inventors have succeeded in obtaining monoclonal antibodies that regulate the cell fusion induced by virus (Ito, Y. et al., J. Virol. 66: 5999–6007 (1992)). These monoclonal antibodies were immunoprecipitated with gp80 and gp135 found on the surface of cells derived from human (Ito, Y. et al., J. Virol. 66: 5999–6007 (1992)). These molecules, gp80 and gp135, were named fusion-regulating proteins, "FRP-1" and "FRP-2", respectively. The present inventors cultured monocytes isolated in the presence of monoclonal antibodies that bind to "FRP-1" protein exposed on the surface of monocytes and found the monoclonal antibodies can differentiate monocytes to osteoclasts. Hence, the method of production of osteoclasts of the present invention comprises a step of contacting monocytes with monoclonal antibody that binds to a portion of "FRP-1" protein exposed on the surface of monocytes.

Any monoclonal antibodies can be used in the method of the present invention as long as they bind to FRP-1 protein exposed on the surface of monocytes and can induce differentiation of monocytes to osteoclasts. The monoclonal antibodies to be used in the method of producing osteoclasts according to the present invention can be prepared by the method well known in the art, for example, Antibodies: A Laboratory Manual (E. Harlow and D. Lane, Cold Spring Harbor Lab., 1988), incorporated by reference. Specific examples of the monoclonal antibodies include 4-5-1, 6-1-13, 4F2, HBJ127, 38-2-2, as described in Ito, Y. et al., J. Virol. 66: 5999–6007 (1992) and Ohgimoto, S. et al., Journal of General Virology 77:2747–2756 (1996) incorporated by reference. The monoclonal antibodies preferably used in the method of the present invention are not limited to these examples, but are selected, for example, by the method of screening a ligand of the present invention as described below.

Monocytes may be isolated by the following method. Namely, peripheral blood monocytes (PBMC) isolated from human blood are suspended in RPMI1640 (GIBCO BRL) supplemented with 10% fetal calf serum (FCS) and allowed to adhere to tissue culture dishes. Adhered cells are recovered to obtain monocytes.

According to the method of the present invention, osteotlasts can be produced by allowing monocytes as isolated above to contact with the above-described monoclonal antibody. Specifically, this step can be carried out by in vitro culture of monocytes which comprises culturing monocytes in a culture medium containing a suitable amount of FCS (for example, RPMI1640 supplemented with 10% FCS) in the presence of the monoclonal antibody. The culturing temperature suitably ranges from 36.5° C. to 37.5° C. Upon culturing, the cell density of monocytes is adjusted to about $1\times10^4$ to $1\times10^5$ cells/ml. The amount of the monoclonal antibody to be used for stimulating monocytes usually ranges from 5 to 10 μg/ml as a final concentration in the culture medium.

Differentiation of monocytes to osteoclasts is induced within about 24 hours after the start of in vitro culture of monocytes in the presence of anti-FRP-1 monoclonal antibody. By further culturing continuously, almost all monocytes can be differentiated to osteoclasts. The culturing time generally ranges from 14 to 28 days though it depends on the monoclonal antibody used. According to the method of the present invention, osteoclasts can be prepared without using other stimulators such as cytokines, interstitial cells, and steroids like 1a,25-dihydroxyvitamin $D_3$, or thyroid hormone.

The present invention also relates to an agent for inducing differentiation of monocytes to osteoclasts, which comprises monoclonal antibody binding to FRP-1 protein as an active ingredient. The agent for induction of in vitro differentiation of monocytes to osteoclasts containing the monoclonal antibody of the present invention may further contain azide, bovine serum albumin, and glycerol, if necessary for preservation. The monoclonal antibody and the other additives if required may be dissolved in water or an appropriate buffer. The agent may be a solution or a lyophilized form.

The use of the monoclonal antibodies binding to FRP-1 protein would enable not only in vitro production of osteoclasts but also differentiation of monocytes to osteoclasts in vivo. Thus, the monoclonal antibodies that bind to FRP-1 protein may be used not only as a reagent for in vitro differentiation of monocytes to osteoclasts but also as a pharmaceutical preparation for treating bone-related diseases such as osteoporosis.

The pharmaceutical preparation comprising the monoclonal antibody may be administered to patients directly or in a dosage form prepared by the known methods together with pharmacologically acceptable carriers or media (for example, sterilized water, physiological saline, vegetable oils, and stabilizers). The administration route includes, for example, intravenous injection, subcutaneous injection, etc., but is not restricted thereto. The dose may vary depending on the body weight and age of the patients. One of ordinary skill in the art would appropriately select an amount effective for the therapy. Generally, it may be within 0.01 and 1000 mg/kg of body weight. The monoclonal antibodies may be humanized by the method known in the art when used in the pharmaceutical composition to reduce antigenicity.

The present invention also relates to a method for screening a ligand that binds to FRP-1 protein. In the above-described method for producing osteoclasts, the binding of the monoclonal antibody to FRP-1 protein on monocytes resulted in induction of differentiation of monocytes to osteoclasts. This fact indicates that differentiation of monocytes to osteoclasts is induced by the interaction between FRP-1 protein and the ligand for FRP-1 protein. Thus, screening of a ligand that binds to FRP-1 protein on the surface of monocytes can be effected utilizing capability to induce differentiation of monocytes to osteoclasts as an index. The screening method of the present invention comprises steps of contacting monocytes with a test sample and detecting differentiation of monocytes to osteoclasts.

The test sample to be used for the screening method of the present invention includes, without limitation, proteins (including antibodies), peptides, gene expression products (including cDNA libraries), non-peptide compounds, extracts from tissues or cells, synthetic compounds, and the like.

The monocytes can be contacted with the test sample by culturing the cells in vitro in the presence of the sample under the same conditions as described above for the method of producing osteoclasts. After culturing the monocytes for a predetermined period, preferably 24 hours or longer, differentiation of monocytes to osteoclasts can be detected, for example, by TRAP (tartrate resistant acid phosphatase) staining, detection of the presence of calcitonin receptor, and detection of bone resorption ability.

The ligand thus isolated may be useful for therapy of bone-related diseases such as osteoporosis. The ligand may be administered as a pharmaceutical preparation to patients as such or as in the dosage form prepared by the known methods together with pharmacologically acceptable carriers or media (for example, sterilized water, physiological saline, vegetable oils, and stabilizers). The administration route may be, for example, intravenous injection, and subcutaneous injection, but is not restricted thereto. The dose varies depending on the body weight and age of patients. One of ordinary skill in the art can select a dose effective for therapy taking the circumstances into consideration. Generally, it may be within 0.01 and 1000 mg/kg of body weight.

As described above, the present invention provides a method of producing osteoclasts which comprises a step of contacting monocytes with monoclonal antibody that binds to a portion of FRP-1 protein exposed on the surface of monocytes. The present invention enables simple production of osteoclasts from monocytes. The present invention also makes it possible to screen a ligand that binds to FRP-1 protein utilizing induction of differentiation of osteoclasts from monocytes as an index. The present invention also provides an agent for induction of differentiation of monocytes to osteoclasts, which comprises monoclonal antibody that binds to FRP-1 protein as an active ingredient. The agent and the above-described ligand are expected to be useful for therapy of bone-related diseases such as osteoporosis.

The following Examples illustrate the present invention in more detail, but are not to be construed to limit the scope of the present invention.

EXAMPLE 1

Isolation of PBMC and Monocytes

PBMC (peripheral blood monocytes) was isolated from the Heparin-treated whole blood from healthy human volunteers by Ficoll-Hipaque density gradient centrifugation. The specific conditions for separation were set up according to the manufacturer's instructions attached to HISTOPAQUE-1077 (SIGMA). PBMC on the interface was collected and suspended in RPMI1640 (GIBCO BRL) containing 10% FCS. The cells were allowed to adhere to tissue culture dishes to obtain adhesive monocytes from PBMC. The purity of the thus-obtained monocytes ($CD14^+$ cells) was about 85 to 90%. The adhesive cells were scraped off with cell scraper instead of EDTA and their survival rate was determined by trypan blue exclusion. As a result, the survival rate was 98% or more. Monocytes were cultured in RPMI1640 containing 10% FCS instead of human serum.

EXAMPLE 2

Induction of Multinucleated Giant Cells by Treating Blood Monocytes with Anti-FRP-1 Monoclonal Antibody First, human blood monocytes (about $1\times10^4$ cells/well) were cultured in the presence of anti FRP-1 monoclonal antibodies (4-5-5-1, 6-1-13, 4F2, HBJ127, 38-2-2) (Ito, Y. et al., J. Virol. 66: 5999–6007 (1992), Ohgimoto, S. et al., Journal of General Virology 77: 2747–2756 (1996)) and morphological changes of monocytes were observed over a suitable period of time. Within 30 minutes, cells began to form small clusters. Aggregation of the cells reached the maximum level after incubation for 2 to 3 hours. The monocytes were treated with anti-FRP-1 monoclonal antibodies other than HBJ127 and, 15 hours thereafter, multinucleated cells appeared. The size of the cells increased up to 3–4 days after the start of incubation with anti-FRP-1 monoclonal antibodies (FIG. 1). Control antibody did not produce distinct effects on monocytes (FIG. 1).

EXAMPLE 3

Figure 2:
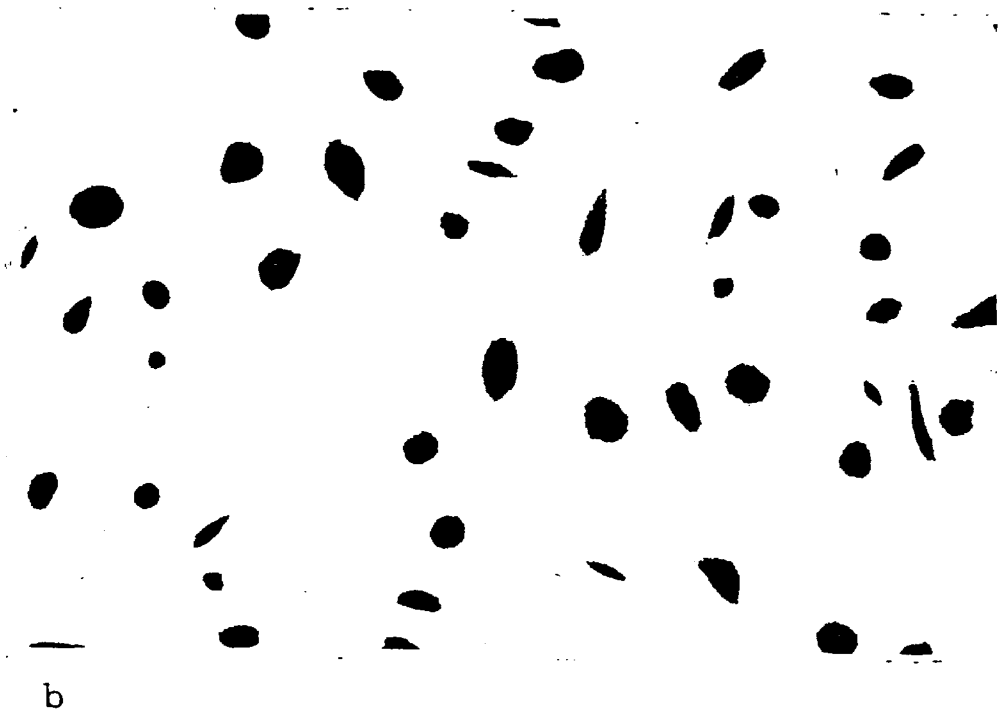
FIG. 2*a* shows TRAP-staining of multinucleated giant cells induced by anti-FRP-1 antibody. Blood monocytes were cultured for 14 days in the presence of anti-FRP-1 antibody (6-1-13; 1 mg/ml) (magnification ×600) followed by TRAP-staining.
FIG. 2*b* shows the total number of multinucleated cells (solid circles connected with solid lines) and the number of TRAP-positive multinucleated cells (bars) among human peripheral blood leucocytes (about $1{\times}10^4$ cells/well) cultured in the presence of anti-FRP-1 antibody (6-1-13; 1 mg/ml).
Figure 2:
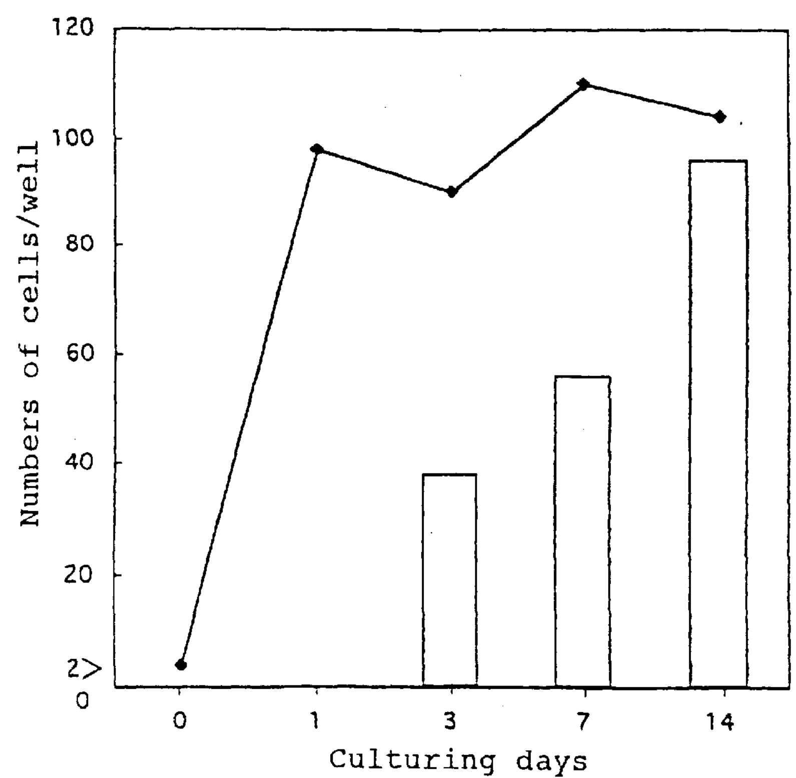

TRAP Staining of Multinucleated Giant Cells Induced by the Anti-FRP-1 Monoclonal Antibody Human blood monocytes were cultured in the presence of anti-FRP-1 monoclonal antibody on the chamber slides and multinucleated giant cells induced by anti FRP-1 monoclonal antibody were subjected to TRAP staining. No TRAP-positive cells appeared up to 24 hours. TRAP-positive multinucleated cells appeared thereafter and 95% of the multinucleated cells became positive after 14 days (FIG. 2*a* and 2*b*). These findings demonstrated that multinucleated giant cells induced by anti-FRP-1 monoclonal antibody became TRAP-positive. A small number of monocytes remained as monocytes after incubation with anti-FRP-1 monoclonal antibody. Almost all of these cells were TRAP-negative, but some of them were TRAP-positive. Neither human monocytes-polykaryon induced by ConA nor syncytia of L929 cells induced by anti-FRP-1 antibody (control polykaryon) was TRAP-positive. In this experiment, TRAP staining was conducted by culturing blood monocytes on chamber slides in the presence of anti-FRP-1 monoclonal antibody and incubating the cells fixed at 37° C. for 30 minutes in an acetate buffer (pH 4) containing naphthol phosphate in the presence of 500 mM tartaric acid. Then, fast violet was added to visualize the products (Sigma Chemical Co., Histochemical Kit 386-A, St. Louis, Mo.).

EXAMPLE 4

Calcitonin Receptors on the Cell Surface of Multinucleated Giant Cells

Calcitonin receptors on the cell surface of multinucleated cells were examined. The presence of calcitonin receptor was confirmed by autoradiography using [$^{125}$I]-human CT (Amersham Japan, IM 175, Tokyo, Japan). Specifically, blood monocytes were cultured on chamber slides for 14 days in the presence of anti-FRP-1 monoclonal antibody, treated with 0.2 nM [$^{125}$I]-CT, and incubated at 37° C. for 2 hours. Labeled CT was allowed to bind to the cells. After washing with cold RPMI1640 containing 10% FCS, the cells were fixed for 10 minutes in a 2% glutaraldehyde-10% formaldehyde solution, subjected to TRAP-staining, and dried. Non-specific binding was confirmed in the presence of excess non-labeled CT (300 nM). Chamber slides were immersed in photographic emulsion and autoradiographed. An excess amount of non-labeled CT (300 nM) was added to negative controls before incubation with 0.2 nM [$^{125}$I]-CT.

As a result, when blood monocytes were cultured for 14 days with anti-FRP-1 monoclonal antibodies, a number of dense grains formed due to binding of [$^{125}$I]-CT were found in TRAP-positive cells as shown in autoradiography (FIG. 3*b*). Addition of an excess amount of non-labeled calcitonin resulted in a complete inhibition of accumulation of the dense grains in the TRAP-positive cells (FIG. 3*a*). These findings reveal that TRAP-positive multinucleated cells have calcitonin receptors (CTR). Calcitonin receptors were scarcely detected in mononuclear cells present in the culture media treated with anti-FRP-1 monoclonal antibodies.

EXAMPLE 5

Bone Resorption Pit Formed by Multinucleated Giant Cells Induced by Anti-FRP-1 Monoclonal Antibody Human cortical bones were prepared and added to 16 mm soft agar well together with blood monocytes and anti-FRP-1 monoclonal antibody (mAb 6-1-13). The cut surface was covered and the part of it was immersed to avoid the outward movement of cells from the pulp. A 1 ml portion of the culture medium was added to each well and incubated at 37° C. for 14 days in 5% $CO_2$ moist air. As a control, the culture medium was incubated under the same conditions as above except for not adding anti-FRP-1 monoclonal antibody. The specimens were fixed in 0.1 M sodium cacodylate buffer (pH 7.2) with a mixture of 2.5% glutaraldehyde and 2%formaldehyde and stained with osmic acid. Then, the specimens were dehydrated in ethanol of gradient concentrations, dried at the critical point with liquid $CO_2$, and spatter-coated with platinum. All specimens were examined with scanning electron microscope.

Figure 4:
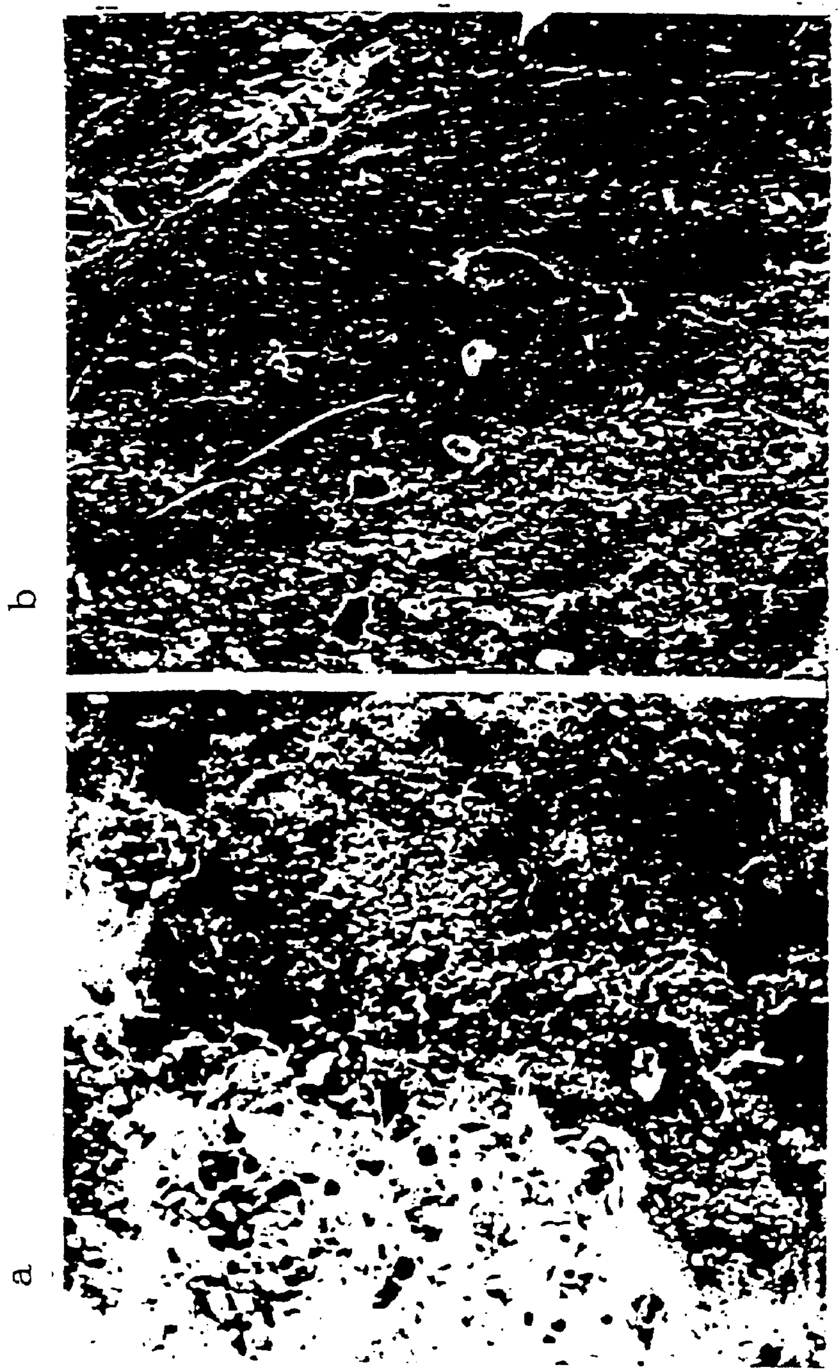
FIG. 4 shows bone resorption pits formed by multinucleated giant cells induced by anti-FRP-1 antibody.

As a result, no resorption occurred when monocytes alone were cultured on the cortical bone slices, while a large number of resorption pit were formed on the surface of the bone slices when monocytes were cultured for 14 days on the cortical bone slices with anti-FRP-1 monoclonal antibody. The resorption pits were distributed on the slices unevenly (FIG. 4). Further, pyridinoline in the monocytes-bone slices culture was measured as biochemical evidence of bone resorption (pyridinoline is a crosslinking substance between collagen molecules as well as deoxypyridinoline and is regarded as one of the markers for bone resorption since it is released upon bone destruction caused during bone resorption). As a result, the amount of pyridinoline in the culture of monocytes-bone resorption slices incubated for 10 days in the absence or presence of anti-FRP-1 antibody was not more than 5 pMOL/ml or not more than 19±4.0 pMOL/ml, respectively (data not shown). These results revealed that multinucleated giant cells induced by anti-FRP-1 monoclonal antibody could effect bone resorption. From the results of Examples 3–5, it is apparent that multinucleated giant cells induced from monocytes are osteoclasts.

EXAMPLE 6

Detection of FRP-1 Antigen on Osteoclasts

Figure 5:
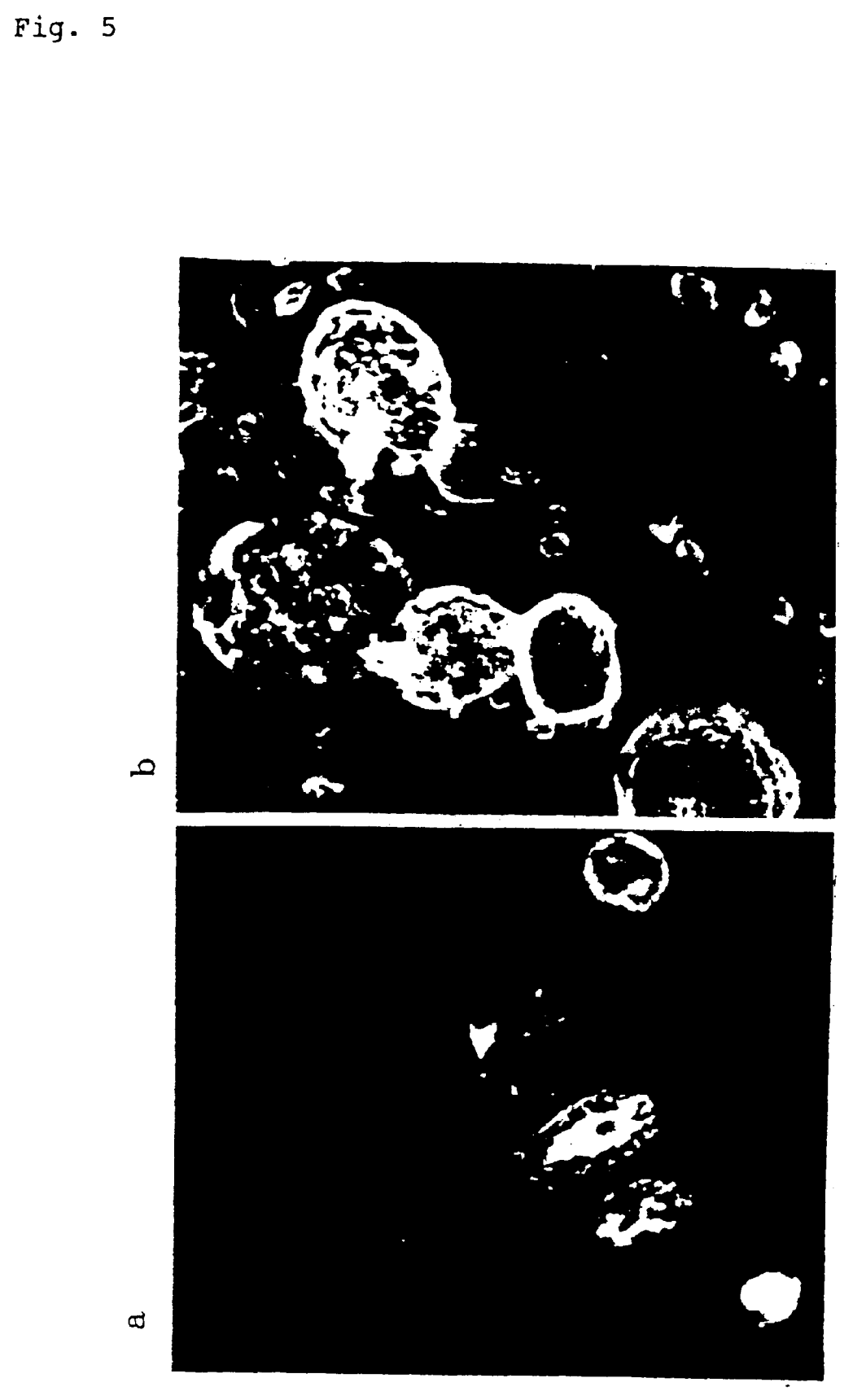

Following the method of Chambers and Manus (Chambers, T. J. and Magnus, C. J., J. Pathology 136: 27–39 (1982)), human osteoclasts were isolated from bone fragments. These cells were TRAP-positive and multinucleated (FIG. 5*a*). Then, human osteoclasts were fixed with 10% paraformaldehyde and stained with anti-FRP-1 monoclonal antibodies (4-5-1). FRP-1 antigens were detected on the osteoclasts isolated from bone fragments (FIG. 5*b*). FRP-1 antigens were also detected in osteoclast-like cells obtained from non-cultured human osteoma.

It has been reported that several kinds of cytokines induce formation of multinucleated cells of monocytes/macrophages (Lacey, D. L. et al., Endocrinol. 136: 2367–2376 (1995), Mundy, G. R. J., Bone and Miner. Res. 8: S505–S510 (1993)). However, production of anyone of cytokines (IL-1a, IL-1b, TNF-a, IL-2, IL-4, IL-6, GM-CSF, G-CSF, IFNa and IFNg) was not increased in the culture of blood monocytes incubated with the anti-FRP-1 monoclonal antibody. It has been reported that M-CSF and its receptor are necessary for formation of normal osteoclasts (Lacey, D. L. et al., Endocrinol. 136: 2367–2376 (1995)). However, anti-M-CSF antibody did not make any influence on the formation of TRAP-positive multinucleated cells induced by the anti-FRP-1 monoclonal antibody. These results indicated that induction of formation of TRAP-positive multinucleated cells (osteoclasts) was caused directly by interaction per se between FRP-1 molecules and the anti-FRP-1 monoclonal antibody (or naturally-occurring ligand to FRP-1) on the surface of monocytes.

Mechanisms for inducing differentiation of osteoclasts from blood monocytes by anti-FRP-1 monoclonal antibody have not been clarified yet. Formation of multinucleated cells from monocytes induced by the anti-FRP-1 antibody was inhibited by anti-β1 integrin antibody, anti-β2 integrin antibody, and fibronectin. However, expression of β1 integrin and β2 integrin was not enhanced by the anti-FRP-1 monoclonal antibody in monocytes (Tabata, N. et al., J. Immun. 153: 3256–3266 (1995)). Thus, formation of multinucleated cells (osteoclasts) from monocytes induced by the anti-FRP-1 antibody may be mediated by activated integrin system.

What is claimed is:

1. A method of producing osteoclasts which comprises a step of contacting monocytes with monoclonal antibody that binds to the fusion regulatory Protein-1 (FRP-1) exposed on the surface of monocytes.

2. A method according to claim 1, wherein said osteoclasts are in vitro cultured cells.

* * * * *

UNITED STATES PATENT AND TRADEMARK OFFICE

CERTIFICATE OF CORRECTION

PATENT NO. : 6,589,528 B2
DATED : July 8, 2003
INVENTOR(S) : Yasuhiko Ito et al.

It is certified that error appears in the above-identified patent and that said Letters Patent is hereby corrected as shown below:

Title page,
Item [56], References Cited, OTHER PUBLICATIONS,
"Ohgimoto et al.," reference, replace "3858" with -- 3585 --.
"Okamato et al.," reference, replace "Okamato" with -- Okamoto --; and replace "Regulator" with -- Regulatory --.
"Roux et al.," reference, replace "Percursors" with -- Precursors --.
"Suga et al.," reference, replace "1/4FR" with -- 1/4F2 --; and replace "CD4" with -- $CD4^+$ --.
"Tabata et al.," reference, replace "-60" with -- α --.
"Udagawa et al.," reference, replace "Osteoclast" with -- Osteoclasts --.

Column 8,
Line 54, replace "in vitro" with -- *in vitro* --.

Signed and Sealed this

Twenty-fifth Day of November, 2003

JAMES E. ROGAN
*Director of the United States Patent and Trademark Office*